United States Patent
Bauer et al.

(10) Patent No.: US 11,401,485 B2
(45) Date of Patent: Aug. 2, 2022

(54) MICROCAPSULE SYSTEM FOR POLYSENSORY OLFACTORY EFFECTS I

(71) Applicant: Henkel AG & Co. KGaA, Duesseldorf (DE)

(72) Inventors: Andreas Bauer, Kaarst (DE); Andre Haetzelt, Eimeldingen (DE); Frank Pessel, Duesseldorf (DE); Andreas Gerigk, Erkelenz (DE); Anneliese Wilsch-Irrgang, Duesseldorf (DE); Klaus Last, Braunschweig (DE); Raul Amado Muñoz, Minden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 112 days.

(21) Appl. No.: 16/616,546

(22) PCT Filed: May 18, 2018

(86) PCT No.: PCT/EP2018/063147
§ 371 (c)(1),
(2) Date: Nov. 25, 2019

(87) PCT Pub. No.: WO2018/215351
PCT Pub. Date: Nov. 29, 2018

(65) Prior Publication Data
US 2021/0163855 A1  Jun. 3, 2021

(30) Foreign Application Priority Data
May 24, 2017 (DE) .......................... 102017111444.0

(51) Int. Cl.
*C11D 3/50* (2006.01)
*B01J 13/08* (2006.01)
*C11D 11/00* (2006.01)
*C11D 17/00* (2006.01)

(52) U.S. Cl.
CPC .............. *C11D 3/505* (2013.01); *B01J 13/08* (2013.01); *C11D 11/0017* (2013.01); *C11D 17/0039* (2013.01)

(58) Field of Classification Search
CPC ......... C11D 3/505; C11D 17/039; A61K 8/11; A61K 2800/654; A61K 9/4816; A61K 9/5073; B01J 13/08
See application file for complete search history.

(56) References Cited

U.S. PATENT DOCUMENTS

| | | | |
|---|---|---|---|
| 3,415,758 A | 12/1968 | Powell et al. | |
| 3,516,941 A | 6/1970 | Matson | |
| 4,406,816 A | 9/1983 | Sliwka | |
| 4,891,172 A | 1/1990 | Matsushita et al. | |
| 6,709,673 B1 | 3/2004 | Tebbe | |
| 2006/0110464 A1* | 5/2006 | Walls | A61K 8/365 424/490 |
| 2007/0122488 A1 | 5/2007 | Windhab et al. | |
| 2013/0203642 A1 | 8/2013 | Huchel et al. | |
| 2014/0178442 A1 | 6/2014 | Li et al. | |
| 2014/0193350 A1 | 7/2014 | Bauer et al. | |
| 2016/0177241 A1 | 6/2016 | Brundel et al. | |

FOREIGN PATENT DOCUMENTS

| | | |
|---|---|---|
| EP | 0026914 A1 | 4/1981 |
| EP | 0967007 A2 | 12/1999 |
| EP | 1097693 A2 | 5/2001 |
| EP | 2732803 A1 | 5/2014 |
| WO | 02060573 A2 | 8/2002 |
| WO | 2004041251 A1 | 5/2004 |
| WO | 2005079968 A1 | 9/2005 |
| WO | 2005079969 A1 | 9/2005 |
| WO | 2012032145 A1 | 3/2012 |
| WO | 2013037575 A1 | 3/2013 |
| WO | 2016200761 A2 | 12/2016 |

OTHER PUBLICATIONS

Hong et al., "Melamine resin microcapsules containing fragrant oil: synthesis and characterization", Material Chemistry and Physics 58, 1999, pp. 128-131.
International search report from parallel PCT Patent Application PCT/EP2018/063147 dated Aug. 28, 2018, 2 pages (for reference purposes only).
International search report from parallel PCT Patent Application PCT/EP2018/063161 dated Sep. 21, 2018, 2 pages (for reference purposes only).

* cited by examiner

*Primary Examiner* — John R Hardee
(74) *Attorney, Agent, or Firm* — Viering Jentschura & Partner MBB

(57) ABSTRACT

A microcapsule system having an outer microcapsule with an outer capsule shell is disclosed. The outer microcapsule comprises at least one inner microcapsule with an inner capsule shell and a first fragrance composition. The inner microcapsule comprises a second fragrance composition that differs from the first fragrance composition. Methods for the production of such micr, products that contain said microcapsules, methods for producing polysensory olfactory impressions and to the corresponding use of the microcapsule system.

14 Claims, No Drawings

MICROCAPSULE SYSTEM FOR POLYSENSORY OLFACTORY EFFECTS I

CROSS-REFERENCE TO RELATED APPLICATION

The present application is a national stage entry according to 35 U.S.C. § 371 of PCT application No.: PCT/EP2018/063147 filed on May 18, 2018; which claims priority to German Patent Application Serial No.: 10 2017 111 444.0, which was filed on May 24, 2017; both of which are incorporated herein by reference in their entirety and for all purposes.

TECHNICAL FIELD

The invention relates to the field of perfume-containing microcapsules, as well as cosmetic agents, cleaning agents and textile treatment agents that contain perfume-containing microcapsules, and methods for releasing fragrances from these microcapsules when said agents are applied.

BACKGROUND

A variety of cosmetic agents, cleaning agents and textile treatment agents contain sensitive ingredients, such as odorants, essential oils, perfume oils and care oils, dyes or antibacterial active ingredients. The disadvantage is that ingredients of this kind used in agents of this kind often lose their activity, or their activity is at least significantly reduced, during storage and/or before the desired application time, specifically for example by chemical reactions caused by interaction with other components of the respective agents and/or by physical influences.

In order for substances of this kind to be used with maximum effect in a controlled manner and at the desired site, active substances such as fragrances, care oils, antibacterial active ingredients and the like are often added to the products in a spatially delimited and protected form. Sensitive substances are often encapsulated in capsules of various sizes, adsorbed on suitable carrier materials, or chemically modified. The substances can then be released by means of a suitable mechanism; for example, they can be released mechanically by shearing, or they can be released directly from the matrix material by diffusion.

There are already numerous commercial encapsulation systems based on natural or artificial polymers. These polymers may enclose an active ingredient or the solution thereof and then be physically or chemically crosslinked in the shell or precipitated by a coacervation process with another polymer. Microcapsules are known from the prior art that may contain liquid, solid or gaseous substances as the core material. Phenol-formaldehyde polymers, melamine-formaldehyde polymers, polyurethane, gelatin, polyamides or polyureas for example are common material for capsule wall. Cosmetic agents, cleaning agents and textile treatment agents containing microcapsules are known per se. In particular, microcapsules consisting of melamine-formaldehyde resins have been found to be suitable in these agents because they are particularly stable.

For example, the European laid-open specification EP 0 967 007 A2 describes a method for microencapsulating biologically active solid substances, in particular pesticides, by the condensation polymerization of a melamine-formaldehyde or phenol-formaldehyde resin or a urea-formalin resin in a dispersion in the presence of the active substance to be encapsulated in each case and a non-ionic polymeric protective colloid for stabilizing the emulsion, with microcapsules having average particle diameters of from 0.1 to 300 μm being obtained. This method is only suitable for the encapsulation of biologically active solid substances. In order to stabilize the emulsion, a polymeric protective colloid has to be added to said emulsion. Conventional capsule systems of a simple shell structure are described.

K. Hong "Melamine resin microcapsules containing fragrant oil: synthesis and characterization" in *Materials Chemistry and Physics* 58 (1999), pages 128-131, describes preparing active ingredient-containing melamine resin microcapsules that have a long shelf life and contain a fragrance oil by in situ polymerization of Migrin oil as the capsule core material, melamine and formalin as the capsule shell material, sodium lauryl sulfate as an emulsifier and polyvinyl alcohol as a protective colloid. This results in capsule systems of a simple shell structure that are loaded with fragrance oil.

Nevertheless, known capsule systems do not allow for different fragrance profiles to be produced over the entire application cycle of a product. This may be desirable or advantageous particularly if the consumer's fragrance impression is intended to change over time. What is conceivable above all here is a first fragrance impression which is characteristic of the product or its intended use and which possibly also creates a certain recognition effect, for example a predominantly cosmetic odor impression when the product is opened or applied which is then replaced by a different odor impression, for example a predominantly fruity odor impression, after application. Therefore, it would be possible, for example, to combine the odor of a washing and cleaning agent product, which is typically intended primarily to impart freshness and cleanliness, with more complex scents that are first released at a later time after application.

SUMMARY

The object of the present invention was therefore to provide the consumer with an improved fragrance experience over the entire application cycle of a product. Such an improvement in odor perception can be achieved by changing odor profiles during the application of a product and/or the use of a surface, for example a textile, provided with the product.

It has now surprisingly been found that the problem can be solved by the use of capsules containing additional smaller fragrance-loaded capsules ("capsule-in-capsule systems") in combination with appropriately formulated fragrance compositions.

In a first aspect, a microcapsule system comprising an outer microcapsule includes an outer capsule shell, the outer microcapsule containing:

a) at least one inner microcapsule enclosed therein having an inner capsule shell; and b) a first fragrance composition;

wherein the capsule shell of the outer microcapsule completely surrounds the inner microcapsule and the first fragrance composition, characterized in that the inner microcapsule contains a second fragrance composition which is completely surrounded by the inner capsule shell of the inner microcapsule and is different from the first fragrance composition.

In a further aspect, methods for producing the microcapsule systems are described herein, comprising (1) providing microcapsules containing the second fragrance composition, and a first fragrance composition, (2) encapsulating the microcapsules containing the second fragrance composition, and the first fragrance composition, in an outer microcapsule.

In yet another aspect, the invention relates to agents for washing, cleaning, conditioning, caring for and/or dyeing hard or soft surfaces, for example textiles, dishes, etc., which agents contain the microcapsule system described herein.

A method for producing polysensory fragrance impressions using the microcapsule systems are described herein, in which the first fragrance composition is first released from the outer microcapsule and then the second fragrance composition is released from the inner microcapsule after a time delay. The first fragrance composition is released, inter alia, by diffusion through the capsule wall of the outer microcapsule and optionally additionally under mechanical stress. The second fragrance composition is released by mechanical force, in particular by friction.

In yet another aspect, the use of the described microcapsule system for producing polysensory fragrance impressions is also disclosed.

Capsule-in-capsule systems are generally known from the international patent publication WO 02/060573 A2, for example. This document describes the encapsulation of a wide range of active substances in capsule-in-capsule systems which can respond to more than one change in environmental properties and which provide good to increased protection for the encapsulated ingredients. The systems described are particularly suitable for use in washing and cleaning agents, cosmetics and body care products, and in adhesive technology. However, no capsule-in-capsule systems are described that are intended for encapsulating at least two different fragrance compositions and that provide for sequential release so as to produce polysensory fragrance impressions.

These and other aspects, features, and advantages of the invention will become apparent to a person skilled in the art through studying the following detailed description and claims. Any feature from one aspect of the invention can be used in any other aspect of the invention. Furthermore, it will readily be understood that the examples contained herein are intended to describe and illustrate, but not to limit, the invention and that, in particular, the invention is not limited to these examples.

Unless indicated otherwise, all percentages indicated are percent by weight and relate to the composition mentioned in each case. Numerical ranges that are indicated in the format "from x to y" also include the stated values. If several preferred numerical ranges are indicated in this format, it is readily understood that all ranges that result from the combination of the various endpoints are also included.

DETAILED DESCRIPTION

"At least one," as used herein, refers to one or more, for example 1, 2, 3, 4, 5, 6, 7, 8, 9 or more. In particular, this expression refers to the type of agent/compound and not to the absolute number of molecules. Therefore, "at least one fragrance" means that at least one type of fragrance is included but also that two or more different types of fragrances may be contained.

"About" or "approximately", as used herein in connection with a numerical value, refers to the numerical value±10%, such as ±5%.

"Microcapsule system," as used herein, refers to the capsule-in-capsule systems described herein, i.e. microcapsules which in turn enclose microcapsules.

"Microcapsule," as used herein, refers to capsules having a core-shell morphology in the micrometer range, comprising a capsule shell which completely encloses a core. "Completely encloses" or "completely surrounds", as used herein with reference to the microcapsules, means that the core is completely surrounded by the shell, i.e. it is not, in particular, embedded in a matrix such that it is exposed at any point. The capsule shell may controllably release the contents, i.e. the contents are not released in a spontaneous and uncontrolled manner, irrespective of any release stimulus. For this reason, the capsule shell is substantially impermeable to the encapsulated contents. "Substantially impermeable," as used in this context, means that the contents of the capsule or individual ingredients cannot spontaneously pass through the shell, but rather the contents can only be released by the capsule being opened or optionally by means of a diffusion process that takes place over a long period of time. The core may be solid, liquid and/or gaseous, but is solid and/or liquid. The microcapsules are substantially spherical and have a diameter in the range of from 0.01 to 1000 µm, in particular from 0.1 to 500 µm. The capsule shell and capsule core are made of different materials; in particular, under standard conditions (20° C., 1013 mbar), the capsule shell is solid, and the core is solid and/or liquid, in particular liquid.

When reference is made in general to "microcapsules" below, it is readily understood that the corresponding statements apply to both the outer microcapsules and the inner microcapsules, unless it is explicitly stated that the statements relate to one of the two types of microcapsules used. Furthermore, it is readily understood that, even when the capsule system is described herein with reference to one outer microcapsule, the microcapsule system used usually contains a plurality of such microcapsules, typically >100, such as >1000, or consists substantially of such microcapsules (i.e. 20 wt. % or more, such as 30 wt. % or more, i.e. 50 wt. % or more), or consists entirely of such capsules (i.e. 100 wt. %). In addition to the microcapsules, the microcapsule system may also comprise a liquid carrier medium, for example an aqueous carrier medium, in which the outer microcapsules are dispersed so as to form, for example, a capsule slurry. In capsule slurries of this kind, the microcapsules typically constitute from 10 to 80 wt. %, from 20 to 50 wt. %.

High-molecular compounds of animal or vegetable origin, e.g. protein compounds (gelatin, albumin, casein), cellulose derivatives (methylcellulose, ethylcellulose, cellulose acetate, cellulose nitrate, carboxymethylcellulose) and in particular synthetic polymers (e.g. polyamides, polyolefins, polyesters, polyurethanes, epoxy resins, silicone resins and condensation products of carbonyl- and NH group-containing compounds), for example, can very generally be used as the capsule material of the microcapsules. Specifically, the shell material may be selected, for example, from polyacrylates; polyethylene; polyamides; polystyrenes; polyisoprenes; polycarbonates; polyesters; polyureas; polyurethanes; polyolefins; polysaccharides; epoxy resins; vinyl polymers; urea crosslinked with formaldehyde or glutaraldehyde; melamine crosslinked with formaldehyde; gelatin-polyphosphate coacervates, optionally crosslinked with glutaraldehyde; gelatin-gum arabic coacervates; silicone resins; polyamines reacted with polyisocyanates; acrylate monomers polymerized by means of free radical polymerization; silk; wool; gelatin; cellulose; proteins; and mixtures and copolymers of the above. Polyacrylates, polyethylene, polyam ides, polystyrenes, polyisoprenes, polycarbonates, polyesters, polyureas, polyurethanes, polyolefins, epoxy resins, vinyl polymers and urea and/or melamine crosslinked with formaldehyde or glutaraldehyde may also be used.

Methods which are in principle suitable for producing the microcapsules are those known microencapsulation methods in which, for example, the phase to be encapsulated is encapsulated by being coated with film-forming polymers (such as those mentioned above) which precipitate on the material to be covered after emulsification and coacervation or interfacial polymerization. The phase to be encapsulated is a fragrance composition, usually in the form of a perfume oil. The inner microcapsules are produced by the aforementioned known methods, by the second fragrance composition, which is usually in the form of a perfume oil, being encapsulated in suitable film-forming polymers. To produce the outer microcapsules, the inner microcapsules are dispersed in the first fragrance composition, which is again usually a perfume oil and which differs from the composition in the inner capsules, and this dispersion is then encapsulated in film-forming polymers.

The microcapsules may release the fragrance compositions contained therein on account of various environmental effects, when the pH or ionic strength of the surroundings changes, when the temperature changes, upon exposure to light, by diffusion and/or under mechanical stress. The outer microcapsule, i.e. the capsule shell of the outer microcapsule, and the inner microcapsule, i.e. the capsule shell of the inner microcapsule, may differ in terms of their construction or composition such that different release mechanisms are used, or different release conditions are used if the same release mechanism is used. "Different release conditions," as used herein, also refers to different permeabilities of the capsule shells, as already defined above. In various embodiments, the outer and inner microcapsules may differ in terms of their release behavior, i.e. the release of the encapsulated material, for example the fragrance compositions. Such a difference in release behavior relates to the capsules as such in direct comparison, i.e. in such a comparison, the inner capsules in a free, unencapsulated form are compared, with respect to release behavior, with the outer capsules as such, i.e. without inner capsules encapsulated therein. In various embodiments, inner and outer capsules differ in terms of their release behavior when a given release mechanism, such as diffusivity, is examined. Such an examination may be performed, for example, by means of thermogravimetric analysis (TGA) at a heating rate of 1 K/min, coupled with fast Fourier infrared spectroscopy (FFIR) in a temperature range of from room temperature (20° C.) to 350° C. in a nitrogen atmosphere (e.g. 1.8 l $N_2$/h). The weight of the capsules is in the range of from 10 to 12 mg, and said capsules are examined in Al crucibles. For the purposes of this comparative test, the two types of capsules are filled with the same fragrance mixture. Before each measurement, a background measurement is taken, the signals of the measurement spectrum always being adjusted immediately by this background. When mentioned herein that inner and outer capsules differ in terms of their release behavior, this means that, unless stated otherwise, the capsules differ in terms of their permeability to the encapsulated substances such that the dynamic phase (i.e. heating) of the TGA-FFIR under the above-mentioned conditions at any time, for example in the temperature range between 80 and 300° C., and at the same temperature results in a difference in weight loss relative to the initial weight of at least 1%. In various embodiments, the weight loss of the outer capsules under the same conditions at the same temperature (for example after 250 minutes of heating at 1 K/m in and a temperature of 280° C.) is at least 1 wt. % greater than that of the inner capsules. This means that, for example, after a period of 250 minutes and at a temperature of 280° C., the weight loss (relative to the initial weight) of the outer capsule is 86.6%, whereas the weight loss of the inner capsule is 82.3% (i.e. a difference of 4.3%).

The first fragrance composition may be released by diffusion and optionally additionally by mechanical release, and for the second fragrance composition to be released by a different release mechanism, in particular only under mechanical stress. For this purpose, it is necessary for the capsule materials of the outer capsule shell and inner capsule shell to be accordingly different. In such embodiments, the outer and inner microcapsules therefore differ on account of their release behavior. In general, the outer microcapsules may slowly release the first fragrance composition, for example by the capsule shell being permeable by diffusion, whereas the inner microcapsules are retained and broken only after a later stimulus. Even though the outer microcapsules are permeable by diffusion, the inner microcapsules are not usually released by diffusion, but rather by the outer microcapsule being broken by one of the other release mechanisms mentioned above. In this case, the difference in diffusivity can also be caused by the inner capsules themselves being encapsulated, meaning that the diffusivity is limited by encapsulation in the outer capsules even if the shell has the same structure. In various embodiments, this difference is however exaggerated further by the fact that the capsule shell of the inner capsules is different from that of the outer capsules, i.e. there is a difference in the release behavior as described above. Thus, when the release mechanism by diffusion is mentioned herein, it always refers to the fragrances, and not the inner microcapsules. "Permeable by diffusion" with reference to the outer capsules means here that the permeability thereof to the fragrance molecules by diffusion is greater than the corresponding permeability of the inner capsules. Therefore, the expression is used herein substantially as a relative concept.

The diffusivity (permeability with respect to diffusion) of the capsules can be adjusted, for example, by the degree of crosslinking of the shell materials and the wall thickness of the capsules.

The microcapsules may be water-soluble and/or water-insoluble microcapsules.

However, the outer microcapsules in particular are water-insoluble microcapsules. The water insolubility of the outer microcapsules has the advantage that, when using appropriate washing or cleaning agents, it is possible for fragrances to stay separated even after application, and that the fragrances can also be released/continue to be released from the microcapsules after application.

The inner microcapsules are also water-insoluble for the reasons set out above. The wall material of the microcapsules comprises polyurethanes, polyolefins, polyamides, polyesters, polysaccharides, epoxy resins, silicone resins and/or polycondensation products of carbonyl compounds and NH group-containing compounds. Melamine-urea-formaldehyde microcapsules or melamine-formaldehyde microcapsules or urea-formaldehyde microcapsules can be used, for example. Thus, in non-limiting embodiments, the outer microcapsules and the inner microcapsules are those based on melamine-formaldehyde resins.

The general approach to producing microcapsules as such has long been known to a person skilled in the art. Particularly suitable methods for producing microcapsules are described in principle in U.S. Pat. Nos. 3,516,941, 3,415,758 or EP 0 026 914 A1, for example. The document mentioned last describes, for example, producing microcapsules by acid-induced condensation of melamine-formaldehyde precondensates and/or the C1-C4 alkyl ethers thereof in water, in which the hydrophobic material forming the capsule core is dispersed, in the presence of a protective colloid.

In non-limiting embodiments, the outer microcapsules are those based on melamine-formaldehyde resins, and the encapsulated fragrances are released at least partially by diffusion. In such embodiments, the capsule shell is permeable to the encapsulated fragrance composition or components thereof such that the odorant molecules are diffused into the ambient air in a long-lasting manner. In addition, the outer microcapsule is breakable under mechanical stress, in particular friable. This mechanism results in the outer capsule shell being broken and thus in the inner capsules being released.

In non-limiting embodiments, the inner microcapsules are those based on melamine-formaldehyde resins and release occurs under mechanical stress; in particular, the inner microcapsules are friable. In such embodiments, the inner microcapsules are substantially impermeable to the encapsulated fragrance composition, i.e. the diffusion of the encapsulated fragrance molecules is limited such that none or only a very small number of the odorant molecules, usually below the perception threshold, pass through the capsule shell by diffusion.

In non-limiting embodiments, the capsule shell of the outer microcapsule is more permeable to the encapsulated first fragrance composition than the capsule shell of the inner microcapsule is to the encapsulated second fragrance composition. In this context, "more permeable" means that the absolute amount of fragrance molecules diffused through the closed shell over a given period of time is greater than the reference. For example, the amount is greater by at least a factor of 2, by at least a factor of 10, or by at least a factor of 100 or 1000. "Permeability" or "diffusion," when used herein, always refers to the capsules after application, i.e. for example after they are absorbed onto a surface, e.g. a textile. Therefore, diffusion occurs into the ambient air, such as from a capsule, which is already largely separated from the other components of the agent in which it was formulated.

In such embodiments, both the outer and inner microcapsules are broken under mechanical stress and the contents are released, but the capsules differ in that the outer microcapsules are partially permeable to the fragrances encapsulated therein, i.e. at least more permeable than the inner microcapsules, such that said fragrances can be released gradually by diffusion, whereas the inner microcapsules are largely impermeable, i.e. less permeable than the outer microcapsules, to the fragrances encapsulated therein, such that said fragrances are only released after the inner capsule shell has broken. However, the outer microcapsules do not allow the inner microcapsules to be released before the outer shell has been broken under mechanical stress. Since the outer microcapsules are broken under mechanical stress, the inner microcapsules are released, which in turn are also broken under mechanical stress. This results in the first fragrance composition that has not already been released by diffusion being released, and at the same time in the second fragrance composition being released. The differences in permeability between outer and inner microcapsules can be measured, for example, as defined above and by means of TGA-FFIR.

The term "friable microcapsules" means those microcapsules which can be opened or abraded by mechanical friction or pressure, e.g. when drying hands on a towel, so that the contents are released only substantially as a result of mechanical action, for example if someone dries their hands on a towel on which such microcapsules are deposited. The melamine-formaldehyde resin-based microcapsules which are used are typically friable microcapsules of this kind.

In various embodiments, capsules for which permeability by diffusion is largely undesirable, such as the inner capsules, have >10 to 20% wall material, such as from 12 to 18%, alternatively from 13 to 17%, i.e. from 14 to 16%, wall material (=shell material), based on the total weight of the capsule, with the remainder being formed by the core material. In combination with a conventional, suitable degree of crosslinking, this leads, for example, to a sufficient diffusion barrier for the inner capsule. The inner capsules therefore have, in various embodiments, a proportion of >10 to 20% wall material, such as from 12 to 18%, alternatively from 13 to 17%, i.e. from 14 to 16%, wall material, relative to the total weight of the capsules.

In various other embodiments, a reduction of >10% in the wall material of the capsule results in increased, faster and more perceptible diffusion of the core material. Accordingly, in various embodiments, the outer capsules are characterized in that, by comparison with the inner capsules, the proportion of the wall material relative to the total weight of the capsules, for the same material and degree of crosslinking, is reduced by more than 10%, for example by >10 to 30%. For example, the inner capsule may have a proportion of wall material of from 14 to 16%, with the outer capsule then having a proportion of wall material of 13% or less, for example from 10 to 12%.

The release behavior may also be controlled by the degree of crosslinking of the capsules, depending on the wall material (the terms "wall material" and "shell material" are used interchangeably herein). In addition to the reaction conditions (e.g. pH, time, temperature), the degree of crosslinking is also determined by the molar ratio of formaldehyde to melamine, in the case of melamine-formaldehyde capsules.

Here, in various embodiments, it has been found that the molar ratio of formaldehyde to melamine can be set at >1:1, for example from 1.05:1 to 1.25:1, for the inner capsule and at <1:1, for example from 0.95:1 to 0.75:1, for the outer capsule in order to achieve the desired differences in release behavior. These differences can be quantified using TGA-FFIR, as described above.

In various embodiments, these features with regard to the amount of wall material and degree of crosslinking are combined, for example by the formaldehyde-melamine ratio, in order to achieve the desired differences in release behavior.

It has surprisingly been found that, when using the capsule systems, the fragrance change leads to a synergistic effect and the fragrance intensity is rated more highly. Furthermore, these capsule-in-capsule systems allow for more pronounced separation of the different fragrances, since the release of the fragrances from the inner capsule, particularly if said capsule is already substantially impermeable to the fragrances, is further impeded by encapsulation in an outer microcapsule. Thus, the odor profile of capsule-in-capsule systems of this kind differs from that in systems in which two different microcapsules each contain scents corresponding to the first and second fragrance compositions and capsule morphologies (i.e. one capsule is permeable by diffusion, whereas the other is substantially impermeable), since the use of two separate capsules always leads to a certain degree of mixing of the individual fragrance compositions, whereas this mixing of the odor impressions is significantly reduced by the claimed capsulein-capsule systems such that the various odors can be perceived as being separated to a more pronounced degree.

Non-limiting microcapsules have an average diameter (median of the size distribution) in the range of between 0.1 and 500 µm, such as between 1 and 150 µm, in particular between 1 and 100 µm, e.g. between 10 and 80 µm. The shell of the microcapsules surrounding the core or the (filled) cavity has an average thickness in the range of advantageously between approximately 1 nm and 1000 nm, such as between approximately 10 nm and approximately 500 nm, alternatively between approximately 30 nm and approximately 300 nm, alternatively between approximately 30 nm and 200 nm, i.e. between approximately 50 nm and approximately 150 nm.

The outer microcapsules have an average diameter (median of the size distribution) of from 5 to 500 µm, such as from 10 to 150 µm, alternatively from 15 to 100 µm with shell thicknesses of from 30 nm to 200 nm, and the inner microcapsules have an average diameter of from 1 to 30 µm, such as from 2 to 25 µm, i.e. from 5 to 20 µm with shell thicknesses of from 30 nm to 200 nm. The permeability of the shell, i.e. the diffusivity, inter alia, can also be controlled by the shell thickness. Small shell thicknesses require a higher permeability by diffusion than larger shell thicknesses. In various embodiments, the shell thickness of the outer microcapsule is approximately less than or equal to that of the inner microcapsule.

In non-limiting embodiments, the outer microcapsule contains on average more than one, such as at least two, alternatively at least three, i.e. four or more, inner microcapsules enclosed therein. In various embodiments, the outer microcapsule may contain up to 20, such as up to 15, i.e. up to 10, inner microcapsules.

In various embodiments, the average diameter of the inner capsules may be smaller than the average diameter of the outer capsules by at least a factor of 2, with said diameter being smaller by a factor of 2-10, in particular 2-5. The outer microcapsules have, for example, an average diameter of from 20 to 80 µm, and the inner microcapsules have an average diameter of from 1 to 20 µm.

The inner microcapsules are dispersed in the first fragrance composition also encapsulated in the outer microcapsules. The capsule shell of both the outer and inner microcapsules is therefore insoluble in the first fragrance composition.

The first and second fragrance compositions each contain at least one fragrance. As fragrances, odorants or perfume oils, all substances and mixtures known for this purpose can be used. The terms "odorant(s)," "fragrances" and "perfume oil(s)" are used synonymously. The terms refer, in particular, to all substances or mixtures thereof that are perceived by humans and animals as having a smell, in particular perceived by humans as having a pleasant smell.

Perfumes, perfume oils, or perfume oil components may be used as fragrance components. Perfume oils or fragrances may be individual odorant compounds, such as synthetic products of the ester, ether, aldehyde, ketone, alcohol, and hydrocarbon types.

Fragrance compounds of the aldehyde type are, for example, adoxal (2,6,10-trimethyl-9-undecenal), anisaldehyde (4-methoxybenzaldehyde), cymene (3-(4-isopropylphenyl)-2-methylpropanal), ethylvanillin, Florhydral (3-(3-isopropylphenyl)butanal), Helional (3-(3,4-methylenedioxyphenyl)-2-methylpropanal), heliotropin, hydroxycitronellal, lauraldehyde, Lyral (3- and 4-(4-hydroxy-4-m ethylpentyl)-3-cyclohexene-1-carboxaldehyde), methylnonylacetaldehyde, Lilial (3-(4-tert-butylphenyl)-2-methylpropanal), phenylacetaldehyde, undecylenealdehyde, vanillin, 2,6,10-trimethyl-9-undecenal, 3-dodecen-1-al, alpha-n-amylcinnamaldehyde, melonal (2,6-dimethyl-5-heptenal), 2,4-di-methyl-3-cyclohexene-1-carboxaldehyde (Triplal), 4-methoxybenzaldehyde, benzaldehyde, 3-(4-tert-butylphenyl)-propanal, 2-methyl-3-(para-methoxyphenyl) propanal, 2-methyl-4-(2,6,6-timethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzylaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, 2,6-dimethyl-5-heptenal, 4-(tricyclo[5.2.1.0(2,6)]-decylidene-8)-butanal, octahydro-4,7-methane-1H-indenecarboxaldehyde, 3-ethoxy-4-hydroxybenzaldehyde, para-ethyl-alpha, alpha-dimethylhydrocinnamaldehyde, alpha-methyl-3,4-(methylenedioxy)-hydrocinnamaldehyde, 3,4-methylenedioxybenzaldehyde, alpha-n-hexylcinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexene carboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methyl-undecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methanindan-1- or 2-carboxaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxaldehyde, 7-hydroxy-3J-dimethyl-octanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexene-carboxaldehyde, 3J-dimethyl-2-methylene-6-octenal, phenoxyacetaldehyde, 5,9-dimethyl-4,8-decadienal, peonyaldehyde (6,10-dimethyl-3-oxa-5,9-undecadien-1-al), hexahydro-4,7-methanindan-1-carboxaldehyde, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propyl-bicyclo-[2.2.1]-hept-5-ene-2-carbaldehyde, 9-decenal, 3-methyl-5-phenyl-1-pentanal, methylnonylacetaldehyde, hexanal and trans-2-hexenal.

Fragrance compounds of the ketone type are, for example, methyl-beta-naphthyl ketone, musk indanone (1,2,3,5,6,7-hexahydro-1,1,2,3,3-pentamethyl-4H-inden-4-one), tonalide (6-acetyl-1,1,2,4,4,7-hexamethyltetralin), alpha-damascone, beta-damascone, delta-damascone, iso-damascone, damascenone, methyldihydrojasmonate, menthone, carvone, camphor, Koavone (3,4,5,6,6-pentamethylhept-3-en-2-one), fenchone, alpha-ionone, beta-ionone, gamma-methyl-ionone, fleuramone (2-heptylcyclopentanone), dihydrojasmone, cis-jasmone, Iso-E-Super (1-(1,2,3,4,5,6J,8-octahydro-2,3,8,8-tetramethyl-2-naphthalenyl)-ethan-1-one (and isomers)), methyl cedrenyl ketone, acetophenone, methyl acetophenone, para-methoxy acetophenone, methyl beta-naphthyl ketone, benzyl acetone, benzophenone, para-hydroxyphenyl butanone, celery ketone (3-methyl-5-propyl-2-cyclohexenone), 6-isopropyldecahydro-2-naphthone, dimethyloctenone, frescomenthe (2-butan-2-yl-cyclohexan-1-one), 4-(1-ethoxyvinyl)-3,3,5,5-tetramethylcyclohexanone, methylheptenone, 2-(2-(4-methyl)-3-cyclohexen-1-yl)propyl)cyclopentanone, 1-(p-menthen-6(2)-yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)-indanone, 4-damascol, Dulcinyl (4-(1,3-benzodioxol-5-yl)butan-2-one), Hexalone (1-(2,6,6-trimethyl-2-cyclohexen-1-yl)-1,6-heptadien-3-one), Isocyclemone E (2-acetonaphthone-1,2,3,4,5,6,7,8-octahydro-2,3,8,8-tetramethyl), methyl nonylketone, methylcyclocitrone, methyl lavender ketone, Orivone (4-tert-amyl-cyclohexanone), 4-tert-butylcyclohexanone, Delphone (2-pentyl-cyclopentanone), muscone (CAS 541-91-3), Neobutenone (1-(5,5-dimethyl-1-cyclohexenyl)pent-4-en-1-one), plicatone (CAS 41724-19-0), Veloutone (2,2,5-trimethyl-5-pentylcyclopentan-1-one), 2,4,4,7-tetramethyl-oct-6-en-3-one and tetramerane (6,10-dimethylundecen-2-one).

Fragrance compounds of the alcohol type are, for example, 10-undecen-1-ol, 2,6-dimethylheptan-2-ol, 2-methylbutanol, 2-methylpentanol, 2-phenoxyethanol, 2-phenylpropanol, 2-tert-butycyclohexanol, 3,5,5-trimethyl-cyclohexanol, 3-hexanol, 3-methyl-5-phenyl-pentanol, 3-octanol, 3-phenyl-propanol, 4-heptenol, 4-isopropylcyclohexanol, 4-tert-butycyclohexanol, 6,8-dimethyl-2-nonanol, 6-nonen-1-ol, 9-decen-1-ol, α-methylbenzyl alcohol, α-terpineol, amyl salicylate, benzyl alcohol, benzyl salicylate, β-terpineol, butyl salicylate, citronellol, cyclohexyl salicylate, decanol, di-hydromyrcenol, dimethylbenzylcarbinol, dimethylheptanol, dimethyloctanol, ethylsalicylate, ethylvanillin, eugenol, farnesol, geraniol, heptanol, hexylsalicylate, isoborneol, isoeugenol, isopulegol, linalool, menthol, myrtenol, n-hexanol, nerol, nonanol, octanol, p-menthan-7-ol, phenylethyl alcohol, phenol, phenyl salicylate, tetrahydrogeraniol, tetrahydrolinalool, thymol, trans-2-cis-6-nonadicnol, trans-2-nonen-1-ol, trans-2-octenol, undecanol, vanillin, champiniol, hexenol and cinnamyl alcohol.

Fragrance compounds of the ester type are e.g. benzyl acetate, phenoxyethyl isobutyrate, p-tert-butylcyclohexyl acetate, linalyl acetate, dim ethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate, and jasmacyclate.

Ethers include, for example, benzyl ethyl ether and Ambroxan. Hydrocarbons mainly include terpenes such as limonene and pinene.

Mixtures of different fragrances are used, which together produce an appealing fragrance note. Such a mixture of fragrances may also be referred to as perfume or perfume oil. Perfume oils of this kind may also contain natural fragrance mixtures, such as those obtainable from plant sources.

Fragrances of plant origin include essential oils, such as angelica root oil, aniseed oil, arnica blossom oil, basil oil, bay oil, champaca blossom oil, citrus oil, abies alba oil, abies alba cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, jasmine oil, cajeput oil, calamus oil, chamomile oil, camphor oil, cananga oil, cardamom oil, cassia oil, pine needle oil, copaiba balsam oil, coriander oil, spearmint oil, caraway oil, cumin oil, labdanum oil, lavender oil, lemon grass oil, lime blossom oil, lime oil, mandarin oil, melissa oil, mint oil, musk seed oil, muscatel oil, myrrh oil, clove oil, neroli oil, niaouli oil, olibanum oil, orange blossom oil, orange peel oil, oregano oil, palmarosa oil, patchouli oil, balsam Peru oil, petitgrain oil, pepper oil, peppermint oil, allspice oil, pine oil, rose oil, rosemary oil, sage oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil and cypress oil, and ambrettolide, Ambroxan, alpha-amylcinnamaldehyde, anethole, anisaldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerianate, borneol, bornyl acetate, boisambrene forte, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmine, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl beta-naphthyl ketone, methyl n-nonylacetaldehyde, methyl n-nonyl ketone, muscone, beta-naphthol ethyl ether, beta-naphthol methyl ether, nerol, n-nonylaldehyde, nonyl alcohol, n-octylaldehyde, p-oxy-acetophenone, pentadecanolide, beta-phenethyl alcohol, phenylacetic acid, pulegone, safrole, salicylic acid isoamyl ester, salicylic acid methyl ester, salicylic acid hexyl ester, salicylic acid cyclohexyl ester, santalol, sandelice, skatole, terpineol, thyme, thymol, troenan, gamma-undecalactone, vanillin, veratraldehyde, cinnamaldehyde, cinnamyl alcohol, cinnamic acid, cinnamic acid ethyl ester, cinnamic acid benzyl ester, diphenyl oxide, limonene, linalool, linalyl acetate and propionate, melusate, menthol, menthone, methyl-n-heptenone, pinene, phenylacetaldehyde, terpinyl acetate, citral, citronellal and mixtures thereof.

different odorants are used, which together produce an appealing fragrance note.

If it is to be perceptible, an odorant must be volatile, wherein, in addition to the nature of the functional groups and the structure of the chemical compound, the molar mass also plays an important role. Therefore, most odorants have molar masses of up to approximately 200 daltons, whereas molar masses of 300 daltons and above represent something of an exception. Due to the differing volatility of odorants, the odor of a perfume or fragrance composed of multiple odorants varies over the course of vaporization, wherein the odor impressions are divided into "top note", "middle note or body" and "end note or dry out." Analogously to the description in the international patent publication WO 2016/200761 A2, the top, middle and end notes can be classified on the basis of their vapor pressure (determinable by means of the test methods described in WO 2016/200761) as follows:

Top notes: vapor pressure at 25° C.: >0.0133 kPa
Middle notes: vapor pressure at 25° C.: 0.0133 to 0.000133 kPa
End notes: vapor pressure at 25° C.: <0.000133 kPa Examples of adherent odorants that can be used are essential oils such as angelica root oil, aniseed oil, arnica blossom oil, basil oil, bay oil, bergamot oil, champaca blossom oil, abies alba oil, abies alba cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajeput oil, calamus oil, chamomile oil, camphor oil, cananga oil, cardamom oil, cassia oil, pine needle oil, copaiba balsam oil, coriander oil, spearmint oil, caraway oil, cumin oil, lavender oil, lemon grass oil, lime oil, mandarin oil, melissa oil, musk seed oil, myrrh oil, clove oil, neroli oil, niaouli oil, olibanum oil, orange oil, oregano oil, palmarosa oil, patchouli oil, balsam Peru oil, petitgrain oil, pepper oil, peppermint oil, allspice oil, pine oil, rose oil, rosemary oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil, and cypress oil.

Higher boiling or solid odorants of natural or synthetic origin include, for example: ambrettolide, α-amylcinnamaldehyde, anethole, anisaldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerianate, borneol, bornyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl-β-naphthyl ketone, methyl n-nonyl acetaldehyde, methyl n-nonyl ketone, muscone, β-naphthol ethyl ether, β-naphthol methyl ether, nerol, nitrobenzene, n-nonyl aldehyde, nonyl alcohol, n-octylaldehyde, p-oxyacetophenone, pentadecanolide, β-phenethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, γ-undecalactone, vanillin, veratraldehyde, cinnamaldehyde, cinnamyl alcohol, cinnamic acid, cinnamic acid ethyl ester and cinnamic acid benzyl ester.

More volatile odorants include in particular lower-boiling odorants of natural or synthetic origin, which may be used alone or in mixtures. Examples of more volatile odorants are alkyl isothiocyanates (alkyl mustard oils), butanedione, limonene, linalool, linayl acetate and propionate, menthol, menthone, methyl-n-heptenone, phellandrene, phenylacetaldehyde, terpinyl acetate, citral and citronellal.

Odorant compounds of the aldehyde type that can be used are hydroxycitronellal (CAS 107-75-5), Helional (CAS 1205-17-0), citral (5392-40-5), bourgeonal (18127-01-0), Triplal (CAS 27939-60-2), Ligustral (CAS 68039-48-5), vertocitral (CAS 68039-49-6), Florhydral (CAS 125109-85-5), citronellal (CAS 106-23-0), citronellyloxyacetaldehyde (CAS 7492-67-3).

In addition to or as an alternative to the above-mentioned odorants, it is also possible to use the odorants described in WO 2016/200761 A2, in particular the odorants mentioned in Tables 1, 2 and 3, and the modulators listed in Tables 4a and 4b. The whole of this publication is incorporated herein by way of reference.

The microcapsules may comprise other oils in addition to odorants. In particular, the microcapsules may also contain active substances in oil form which are suitable for washing, cleaning, caring and/or finishing purposes, in particular
a) textile care substances, such as silicone oils, and/or
b) skin care substances, such as vitamin E, natural oils and/or cosmetic oils.

Skin care active substances are all those active substances which give the skin a sensory and/or cosmetic advantage. Skin care active substances are selected from the following substances:
a) waxes such as carnauba, spermaceti, beeswax, lanolin and/or derivatives thereof and others
b) hydrophobic plant extracts
c) hydrocarbons such as squalene and/or squalane
d) higher fatty acids, such as those having at least 12 carbon atoms, for example lauric acid, stearic acid, behenic acid, myristic acid, palmitic acid, oleic acid, linoleic acid, linolenic acid, isostearic acid and/or polyunsaturated fatty acids and others.
e) higher fatty alcohols, such as those having at least 12 carbon atoms, for example lauryl alcohol, cetyl alcohol, stearyl alcohol, oleyl alcohol, behenyl alcohol, cholesterol and/or 2-hexadecanol and others.
f) esters, such as cetyloctanoate, lauryl lactate, myristyl lactate, cetyl lactate, isopropyl myristate, myristyl myristate, isopropyl palmitate, isopropyl adipate, butyl stearate, decyl oleate, cholesteryl isostearate, glycerol monostearate, glyceryl distearate, glycerol tristearate, alkyl lactate, alkyl citrate and/or alkyl tartrate and others.
g) lipids such as cholesterol, ceram ides and/or sucrose esters and others
h) vitamins such as vitamins A, C and E, vitamin alkyl esters, including vitamin C alkyl esters and others.
i) sunscreens
j) phospholipids
k) derivatives of alpha hydroxy acids
l) germicides for cosmetic use, both synthetic such as salicylic acid and/or others and natural such as neem oil and/or others.
m) silicones
n) natural oils, e.g. almond oil
and mixtures of any of the components listed above.

In various embodiments, the microcapsules additionally contain plant extracts as an active substance. These extracts are typically prepared by extraction of the entire plant. It may also be in some cases, however, to prepare the extracts solely from the flowers and/or leaves of the plant.

Extracts from green tea, oak bark, stinging nettle, witch hazel, hops, henna, chamomile, burdock root, horsetail, whitethorn, lime blossom, almond, aloe vera, spruce needles, horse chestnut, sandalwood, juniper, coconut, mango, apricot, lemon, wheat, kiwi, melon, orange, grapefruit, sage, rosemary, birch, mallow, cuckoo flower, wild thyme, yarrow, thyme, melissa, restharrow, coltsfoot, marshmallow, meristem, ginseng and ginger root are particularly suitable.

Water, alcohols, and mixtures thereof can be used as extracting agents for preparing the mentioned plant extracts. Of the alcohols, low alcohols such as ethanol and isopropanol, such as polyhydric alcohols such as ethylene glycol and propylene glycol, may be used, both as the sole extracting agent and in a mixture with water. Plant extracts based on water/propylene glycol in the ratio of 1:10 to 10:1 have been found to be particularly suitable.

The plant extracts can be used both in pure form and in diluted form. If they are used in diluted form, they typically contain approximately 2 to 80 wt. % active substance and the extracting agent or extracting agent mixture used for their extraction as the solvent.

It may also be possible to use several, in particular two, different plant extracts as the active substance.

It may be advantageous for the outer/inner microcapsules that can be used to be absorbed particularly easily onto the treated textile. This is achieved, for example, by using aminoplast capsules, such as those based on melamine-formaldehyde. After the washing process, aminoplast capsules of this kind in particular typically have a certain brittleness such that, by the action of mechanical force, the active substances, in particular fragrances, can be purposely released from the capsule, e.g. when rubbing skin on a towel which has been washed using an appropriate washing agent. This makes it possible for a pleasant smell, for example, to be purposely produced even after the laundry has been stored for a long time. Said purposely produced pleasant smell differs from the odor of the product, which is produced substantially by the conventional scent and by the use of outer microcapsules that are permeable by diffusion and the first fragrance composition, since said odor is dominated by the second fragrance composition released from the inner microcapsule, optionally in combination with the residues of the first fragrance composition released simultaneously from the outer microcapsules. This provides for a polysensory fragrance experience, i.e. an odor experience which is characteristic of the product as such and occurs during opening or application is subsequently replaced by a later odor experience which occurs only after application. The consumer is thus able to purposely produce pleasant smells that differ from the odor of the washing agent.

In particular, the separation of the different fragrance compositions in different microcapsules offers the advantage of providing for a comparatively pronounced separation of the perceived fragrance of the different compositions, and is far superior to known methods based on the mixture of fragrances having different volatilities.

The first and second fragrance compositions differ, for example, in terms of their fragrance profile and/or the volatility of the contained fragrances and/or the substantivity of the contained fragrances. The fragrance profiles of the first fragrance composition and second fragrance composition may be perceived differently by the consumer with respect to the senses. Fragrance profiles may be described, for example, as fresh, green, ozone, floral, rose, lily of the valley, fruity, apple, berry, citrus, woody, cosmetic, balsamic, amber, musk and fougere amongst others. Additionally or alternatively, the two fragrance compositions in the outer and inner capsules can also differ in terms of physicochemical composition, i.e. the fragrances/fragrance mixtures used differ in terms of composition and physical parameters, such as vapor pressure, boiling point, hydrophobicity (cLogP value), etc.

In various embodiments, to that effect, the first and second fragrance compositions differ in that the first fragrance composition contains at least one fragrance, such as two fragrances, alternatively three fragrances, i.e. four or more fragrances that are not contained in the second fragrance composition. Likewise, the second fragrance composition may contain at least one fragrance, such as two fragrances, alternatively three fragrances, i.e. four or more fragrances that are not contained in the first fragrance composition. However, it is not excluded that both fragrance compositions contain the same fragrances, as long as the compositions differ by at least one fragrance and/or in the amounts of the fragrances used.

Generally, in various embodiments, the second fragrance composition, i.e. the composition in the inner capsule, may perform better than the first fragrance composition. As a result, the odor profile of the second fragrance composition dominates, even with partially simultaneous release, for example when residues of the first fragrance composition are released, by friction, together with the second fragrance composition. Methods for achieving this are known to a person skilled in the art, for example the selection of odorants on account of their vapor pressures.

The microcapsule systems described herein contain the fragrance compositions in an amount of from 0.1 to 95 wt. %, such as from 1 to 90 wt. %, i.e. from 5 to 85 wt. %, based on the total microcapsule system. The first fragrance composition constitutes at least 30 wt. %, such as at least 50 wt. %, up to, for example, 80 wt. % or up to 70 wt. %, of the total amount of fragrance compositions in the capsule system. In various embodiments, the weight of the inner microcapsules constitutes up to 60 wt. %, such as from 1 to 50 wt. %, i.e. from 2 to 40 wt. %, of the total microcapsule system. In various embodiments, the weight of the polymer from which the outer capsule shell is made constitutes from 1 to 25 wt. %, in particular from 5 to 20 wt. %, of the total weight of the microcapsule system.

The microcapsule systems may be present in known forms, for example as a slurry in an aqueous carrier medium or as a powder.

The agents for washing, cleaning, conditioning, caring for and/or dyeing hard or soft surfaces contain microcapsules in amounts of from 0.0001 to 50 wt. %, such as from 0.01 to 20 wt. %, and in particular from 0.1 to 5 wt. %, based on the total agent.

Within the meaning of this application, the agents for washing, cleaning, conditioning, caring for and/or dyeing hard or soft surfaces are washing agents, cleaning agents, post-treatment agents and/or cosmetic agents.

The agents are used for washing, cleaning, conditioning, caring for and/or dyeing hard or soft surfaces. Within the meaning of this application, hard surfaces are windows, mirrors and other glass surfaces, surfaces made of ceramic, plastics material, metal or wood and lacquered wood, which are found in the household and commercial sectors, such as bathroom ceramics, cooking and dining utensils, kitchen surfaces or floors. Within the meaning of this application, soft surfaces are textile sheet materials, skin and hair.

Within the meaning of this application, agents for washing hard or soft surfaces are textile washing agents, for example formulations in the form of powders, granules, beads, tablets, pastes, gels, wipes, bars or liquids.

Within the meaning of this application, agents for cleaning hard or soft surfaces include all cleaners for hard or soft surfaces, in particular dishwashing detergents, all-purpose cleaners, toilet cleaners, sanitary cleaners and glass cleaners, toothpastes, skin washing agents, such as shower gels, or hair washing agents.

Within the meaning of this application, agents for conditioning hard or soft surfaces are fabric softeners, rimblocks, conditioning wipes for use in tumble dryers, hygiene rinsers, deodorants, antiperspirants, hair conditioners, styling agents and/or hair setting agents.

Within the meaning of this application, agents for caring for hard or soft surfaces are textile care products, hair care products or skin treatment agents, such as creams, lotions or gels.

Within the meaning of this application, agents for dyeing hard or soft surfaces are hair dyeing and hair toning agents and agents for lightening keratin fibers.

In addition to the capsule-in-capsule systems described herein, the agents may additionally contain a conventional scent. This differs from both the first fragrance composition and second fragrance composition of the systems, for example in terms of the parameters discussed above. This conventional scent can give the product as such the actual odor which is perceived during opening/application. In addition, the agents may also contain other conventional perfume microcapsules containing the same or different scents.

The agents for washing, cleaning, conditioning, caring for and/or dyeing hard or soft surfaces provide for the targeted release of odorants stored in the outer/inner capsules, but at the same time have their own odor, typically determined by a conventional scent of the product. The outer/inner capsules are stable within the agent matrix and can be opened by a targeted stimulus, in particular mechanical force, the outer capsules additionally allowing the odorants to be released by means of diffusion. Mechanical force is understood to mean any type of force applied to the microcapsule, such as shearing forces, pressure and/or friction. When the agent is applied, for example for textile washing or skin cleansing, the outer microcapsules are deposited on the hard or soft surface. The fragrances are then released from the outer microcapsules by diffusion, i.e. the fragrances migrate through the polymeric shell material and are thus released slowly. After the surface has dried, the microcapsules can be easily opened, e.g. by friction, the friction also opening the inner microcapsules thus released from the outer microcapsules. In this way, the fragrance(s) of the residues of the first fragrance composition are released in a targeted manner from the outer capsules (the portion that has not already been released by diffusion) and the second fragrance composition is released in a targeted manner from the inner capsules, such that the performance profile of the entire agent is enhanced. In particular, the fragrance effect is of particular importance, since the consumer often judges product performance proportionally to the pleasant smell.

The agents for washing, cleaning, conditioning, caring for and/or dyeing hard or soft surfaces described herein provides for long-lasting fragrance release, in particular long-lasting fragrancing and care of hard or soft surfaces (by the release from the outer microcapsule) and a targeted fragrance release (by the release from the inner microcapsule and optionally also the outer microcapsule) even after long time intervals by using the microcapsule systems described herein.

In a non-limiting embodiment, the surface is a textile surface. When the surface is a textile surface, the agent for washing, cleaning, conditioning, caring for and/or dyeing hard or soft surfaces may be a washing agent, cleaning agent or post-treatment agent.

In a further embodiment, the surface is a body part, in particular skin and/or hair. When the surface is a body part, in particular skin and/or hair, the agent for washing, cleaning, conditioning, caring for and/or dyeing hard or soft surfaces may be a cosmetic composition.

The microcapsules can be brought into contact with the skin and/or hair either by the skin and/or hair being brought into direct contact with a cosmetic composition comprising microcapsules and/or by conveying the microcapsules through textiles carrying microcapsules of this kind on the surface.

In the methods also described herein for producing the microcapsule systems, first the inner microcapsules containing the second fragrance composition are produced using methods known from the prior art. These are then mixed with the first fragrance composition, dispersed therein, and the resulting mixture is encapsulated using known methods so as to form the outer microcapsules.

The microcapsules containing the second fragrance composition may be surface modified to facilitate encapsulation in the outer microcapsule. For this purpose, the microcapsules containing the second fragrance composition (inner microcapsules) are suspended in water, for example with one or more hydrophobic modifiers. The modifiers may be at least one compound selected from the group consisting of polyethyleneim ides, quaternary ammonium compounds, those having hydrophobic hydrocarbon functional groups, quaternary polyvinylpyrrolidones and unsaturated fatty acids such as oleic acid. Examples of suitable quaternary ammonium compounds are betaine, choline chloride, benzalkonium chloride and di-($C_{8-18}$ alkyl)dimethyl ammonium chloride, such as didecyldimethylammonium chloride. Suitable polyethyleneimide compounds are multifunctional ethyleneimide-based cationic polymers having molar masses in the range of from 600 to 2,500,000 Da. Such polymers are commercially available, for example, from BASF SE under the trade name Lupasol. Likewise, suitable quaternary PVPs are commercially available from BASF SE under the trade name Luviquat. In general, corresponding methods for surface modification and encapsulation are described, for example, in EP 2 732 803 A1 for "disintegrants" and are readily transferable to the inner microcapsules. After modification, the microcapsules may be dried before being combined with the first fragrance composition and encapsulated in the outer microcapsule.

It goes without saying that the surface-modified inner microcapsules described above in the context of the methods can also be used in the microcapsule systems. In various embodiments, the inner microcapsules are therefore surface-modified microcapsules as described above, in particular those which have been hydrophobically modified, such as those modified with at least one modifier selected from the group consisting of polyethyleneimides, quaternary ammonium compounds, quaternary polyvinylpyrrolidones and oleic acid.

By selecting and controlling the reaction conditions when forming the shells, for example by controlling the shell thickness, the permeability thereof to the encapsulated odorants can be controlled. This makes it possible, for example, to produce inner microcapsule shells that are impermeable to the encapsulated odorants, and outer microcapsule shells that allow release by diffusion through the capsule shell.

Methods for producing polysensory fragrance impressions using the microcapsule systems are described herein. In these methods, the first fragrance composition is first released from the outer microcapsule and then the second fragrance composition is released from the inner microcapsule after a time delay. As a result, the fragrance profile can be modified and a polysensory fragrance impression for the consumer can be produced. The fragrance experience can be broadened by additionally using a conventional, i.e. non-encapsulated, scent in the agent. As a result, when opening and applying the product, there is a first fragrance impression substantially caused by the conventional scent, and as the application cycle continues the first fragrance composition is released from the outer microcapsules by diffusion, and finally the second fragrance composition is released from the inner microcapsules under mechanical stress.

In various embodiments of this method, the agent in which the capsule system described herein is used is a textile treatment agent, such as a detergent or softener, which additionally contains a conventional perfume. The capsule system used is based on melamine-formaldehyde resin, with the outer capsule being permeable by diffusion and the inner capsule being closed, but with both being friable. In a first step, before the product is applied, the top and middle notes of the conventional scent are released from the product, thus providing a first fragrance impression. After application, a wet textile is obtained which is olfactorily characterized by the top and middle notes of the conventional scent and the fragrance composition released by diffusion from the outer capsule. The dry textile is characterized by the middle and end notes of the conventional scent and the fragrance composition released by diffusion from the outer capsule, and after mechanical stress, for example by friction or the wearing of the textile, the scent is released from the inner capsule and becomes dominant. It goes without saying that, in the course of the application cycle, the odor profile of the conventional perfume rapidly weakens and is gradually replaced by the odorants released by means of diffusion from the outer microcapsule. These are then replaced by the odorants from the inner microcapsule under mechanical stress, i.e. when using or wearing the dry textile.

In this way, the microcapsule systems described herein can be used to produce polysensory fragrance impressions.

The embodiments described in connection with the capsule systems are also transferable to methods for the production thereof, the agents containing them and the uses and methods described herein, and vice versa.

The invention is described in the following with reference to examples, but is not limited to these examples.

EXAMPLES

Example 1

A commercially available softener (Vernel conc.) or detergent (Persil powder) was mixed with a capsule system (sample 2; 0.3 wt. % melamine-formaldehyde capsule slurry: inner capsule closed, friable and loaded with perfume 3, outer capsule diffusive, friable and loaded with perfume 2) or a conventional capsule system (sample 1; 0.15 wt. % melamine-formaldehyde capsule slurry: capsule closed, friable and loaded with perfume 3; 0.15 wt. % melamine-formaldehyde-capsule-slurry: capsule diffusive, friable and loaded with perfume 2) and used according to instructions for washing textiles (Miele Softtronic W1734, main wash cycle at 40° C., spin speed at 1200 rpm, water hardness at 12° dH, 3.5 kg cotton terry cloth per wash cycle). Subsequently, a panel of trained perfumers assessed by smell the textiles in a dry state before and after friction and in a wet state by comparison with the dry state, and the fragrance change was assessed on a scale of 1-5 (1=unchanged; 2=slight change in the fragrance profile by comparison with the reference; 3=moderate change; 4=great change; 5=total change) and the fragrance intensity was assessed on a scale of 1-10 (1=odorless, 10=very intense).

Assessment of fragrance change of dry laundry before/after friction (after washing with softener+microcapsules and drying)

|  | Dry laundry before friction | Dry laundry after friction |
| --- | --- | --- |
| Sample 1 | Reference | Reference |
| Sample 2 | 3.2 | 4.2 |

In the case of dry laundry before friction, there is already a moderate change in the odor profile by comparison with the reference system in which two separate capsules are used. The reason for this is that in the reference system, even with different permeabilities of the capsule shells, the two fragrance compositions are nevertheless always released to such an extent that the fragrance impression is the result of a mixture of the two encapsulated compositions (i.e. larger proportions from the diffusely permeable capsule and smaller proportions from the substantially impermeable capsule). By contrast, the capsule-in-capsule system is advantageous because the fragrance impression of the dry laundry is even more dominated by the first fragrance composition because the release from the inner capsule is hindered not only by the less permeable capsule wall, but also by the encapsulation in the outer microcapsule. This difference is therefore due to the substantial difference between the odor profiles of the two microcapsule systems tested. This difference is further exaggerated in the dry laundry after friction in that the odor profile is even more dominated by the composition in the inner (less permeable) capsule.

Assessment of Fragrance Intensity of Dry Laundry Before/after Friction (after Washing with Softener+Microcapsules and Drying)

|  | Dry laundry before friction | Dry laundry after friction |
| --- | --- | --- |
| Sample 1 | 7.6 | 8.0 |
| Sample 2 | 7.9 | 9.2 |

Assessment of Fragrance Change of Wet Laundry/Dry Laundry (after Washing with Softener+Microcapsules and Optional Drying)

|  | Wet laundry before friction | Dry laundry before friction |
| --- | --- | --- |
| Sample 1 | Reference | Reference |
| Sample 2 | 2.6 | 3.2 |

Assessment of Fragrance Intensity of Dry/Wet Laundry (after Washing with Softener+Microcapsules and Optional Drying)

|  | Wet laundry before friction | Dry laundry before friction |
| --- | --- | --- |
| Sample 1 | 8.2 | 7.6 |
| Sample 2 | 8.6 | 7.9 |

Assessment of Fragrance Change of Dry Laundry Before/after Friction (after Washing with Detergent+Microcapsules and Drying)

|  | Dry laundry before friction | Dry laundry after friction |
| --- | --- | --- |
| Sample 1 | Reference | Reference |
| Sample 2 | 2.8 | 3.4 |

Assessment of Fragrance Intensity of Dry Laundry Before/after Friction (after Washing with Detergent+Microcapsules and Drying)

|  | Dry laundry before friction | Dry laundry after friction |
| --- | --- | --- |
| Sample 1 | 6.4 | 7.6 |
| Sample 2 | 7.2 | 8.2 |

As already discussed in detail above, in the case of sample 2, what is generally apparent is a higher separation precision of the fragrance profiles before and after friction and in wet and dry laundry.

The invention claimed is:

1. A microcapsule system comprising an outer microcapsule having an outer capsule shell, wherein the outer microcapsule comprises:
   at least one inner microcapsule enclosed therein having an inner capsule shell; and
   a first fragrance composition; and
wherein the outer capsule shell of the outer microcapsule completely surrounds the inner microcapsule and the first fragrance composition; wherein the outer capsule shell is at least partially permeable to parts of the first fragrance composition and said parts are releasable by diffusion; wherein the outer shell has a thickness ranging from 30 nm to 200 nm;
wherein the inner microcapsule comprises a second fragrance composition which is completely surrounded by the inner capsule shell of the inner microcapsule; wherein the second fragrance composition is releasable from the inner capsule under mechanical stress; wherein the inner shell has a thickness ranging from 30 nm to 200 nm; and wherein the second fragrance composition is different from the first fragrance composition.

2. The microcapsule system according to claim 1, wherein the outer microcapsule comprises on average more than one inner microcapsule enclosed therein.

3. The microcapsule system according to claim 1, wherein the inner capsule shell is less permeable to the second fragrance composition than the outer capsule shell is to the first fragrance composition.

4. The microcapsule system according to claim 1, wherein the first fragrance composition and the second fragrance composition differ with regard to their fragrance profile and/or physicochemical properties.

5. The microcapsule according to claim 1, wherein the inner microcapsule shell comprises a melamine-formaldehyde resin.

6. The microcapsule system according to claim 1, wherein the outer capsule shell is water-insoluble or the inner capsule shell is water-insoluble or both.

7. The microcapsule system according to claim 1, wherein the inner capsule shell is substantially impermeable to the second fragrance composition.

8. The microcapsule system according to claim 1, wherein the outer microcapsule shell has an amount of shell material ranging from 10% to 12% relative to the total weight of the microcapsule, and wherein the inner microcapsule shell has an amount of shell material ranging from 14% to 16% relative to the total weight of the microcapsule.

9. A method for producing a microcapsule system according to claim 1, wherein the method comprises:
   providing microcapsules containing the second fragrance composition, and a first fragrance composition; and
   encapsulating the microcapsules containing the second fragrance composition, and the first fragrance composition, in an outer microcapsule.

10. An agent composition for washing, cleaning, conditioning, caring for and/or dyeing hard or soft surfaces, containing the microcapsule system according to claim 1.

11. A microcapsule system comprising an outer microcapsule having an outer capsule shell, wherein the outer microcapsule comprises:
    at least one inner microcapsule enclosed therein having an inner capsule shell; and
    a first fragrance composition; and
    wherein the outer capsule shell of the outer microcapsule completely surrounds the inner microcapsule and the first fragrance composition; wherein the outer capsule shell is at least partially permeable to parts of the first fragrance composition and said parts are releasable by diffusion; wherein the outer shell has a thickness ranging from 30 nm to 200 nm;
    wherein the inner microcapsule comprises a second fragrance composition which is completely surrounded by the inner capsule shell of the inner microcapsule; wherein the second fragrance composition is releasable from the inner capsule under mechanical stress; wherein the inner shell has a thickness ranging from 30 nm to 200 nm; and wherein the second fragrance composition is different from the first fragrance composition; wherein the inner capsule shell is friable.

12. The microcapsule system according to claim 11, wherein the outer capsule shell is friable.

13. The microcapsule system according to claim 11, wherein the outer capsule shell is water-insoluble or the inner capsule shell is water-insoluble or both.

14. The microcapsule system according to claim 11, wherein the inner capsule shell is substantially impermeable to the second fragrance composition.

* * * * *